US00PP07941P

United States Patent [19]

Warriner

[11] Patent Number: Plant 7,941

[45] Date of Patent: Aug. 18, 1992

[54] ROSE PLANT JACFLARE

[75] Inventor: William A. Warriner, Tustin, Calif.

[73] Assignee: Bear Creek Gardens, Inc., Medford, Oreg.

[21] Appl. No.: 625,872

[22] Filed: Dec. 10, 1990

[51] Int. Cl.[5] ..... A01H 5/00

[52] U.S. Cl. ..... Plt./8.2

[58] Field of Search ..... Plt./8, 8.2

*Primary Examiner*—Howard J. Locker

*Attorney, Agent, or Firm*—Klarquist, Sparkman, Campbell, Leigh and Whinston

[57] ABSTRACT

A miniature class rose plant having a compact miniature growth, bright deep yellow flowers, dark glossy green foliage, resistance to rust and powdery mildew, and continuous flower production during the growing season.

1 Drawing Sheet

The present invention relates to a new and distinct variety of rose plant of the miniature class which was originated by me by crossing an unnamed miniature variety with the variety Sunflare, U.S. Plant Pat. No. 5,001.

The primary objective of this breeding was to produce a new rose variety having the dwarf habit of the light yellow, miniature, unnamed variety combined with the bright yellow of Sunflare flowers coupled with the bright green, disease-resistant foliage of Sunflare. The objective was substantially achieved along with other desirable improvements as evidenced by the following unique combination of characteristics which are outstanding in the new variety and which distinguish it from its parents, as well as from all other varieties of which I am aware:

1. A compact miniature growth.
2. Bright, deep yellow flowers.
3. Dark, glossy green foliage.
4. Resistance to rust and powdery mildew.
5. Continuous flower production during the growing season.

Asexual reproduction of this new variety by budding, as performed at Wasco, Calif., shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color description using terminology in accordance with The Royal Horticultural Society (London) Colour Chart, except where ordinary dictionary significance of color is indicated.

Parentage:

*Seed parent.*—Unnamed miniature variety.

*Pollen parent.*—Sunflare, U.S. Plant Pat. No. 5,001.

Classification:

*Botanical.*—*Rosa hybrida.*

*Commercial.*—Miniature.

FLOWER

Observations made from specimens grown in a garden in Somis, Calif., in Sep., 1990.

Blooming habit: Continuous.

Bud:

*Size.*—½ inch when the petals start to unfurl.

*Form.*—Short, pointed ovoid.

*Color.*—When sepals first divide, bud color is Yellow Orange 15B. When half blown, the upper sides of the petals are Yellow Orange 15B; and the lower sides of the petals are Yellow Orange 15B.

*Sepals.*—Color: Green Group 138B. Surface texture: Covered with fine hairs. There are three lightly appendaged sepals. There are two unappendaged sepals with hairy edges with occasional glands.

*Receptacle.*—Color: Green Group 137C. Shape: Funnel. Size: Small (¼×¼"). Surface: Hairy.

*Peduncle.*—Length: Short (1 to 1¼"). Surface: Smooth but covered with very fine hairs and glandular. Color: Medium green. Strength: Stiff, erect.

Bloom:

*Size.*—Small. Average open size is 1½ inches.

*Borne.*—Singly and several together, in rounded to flat clusters.

*Stems.*—Short, strong.

*Form.*—When first open: High center. Permanence: Retains its form to the end; outer petals curl back, quill fashion.

*Petalage.*—Number of petals under normal condition: 30 to 35.

*Color.*—The upper side of the petals is Yellow Orange Group 15B. The reverse side of the petals is Yellow Orange Group 15B. The base of petals is Yellow Orange 15B, with no distinctive coloration at the point of attachment. The major color on the upper side is Yellow Orange 15B.

*Variegations.*—None.

*Discoloration.*—No change in the general tonality at the end of the first day. No change at the end of the third day.

*Fragrance.*—Slight.

Petals:

*Texture.*—Thin.

*Shape.*—Deltoid.

*Form.*—Moderately quilled.

*Arrangement.*—Imbricated. Petaloids in the center: Few.

*Persistence.*—Drop off cleanly.

*Lastingness.*—On the plant: Fair (3 to 5 days). As a cut flower: Long (5 to 7 days).

Reproductive parts:

*Anthers.*—Size: Medium. Quantity: Many. Color: Yellow. Arrangement: Regular around styles, mixed with occasional petaloids.

*Filaments.*—Color: Yellow.

*Pollen.*—Color: Gold yellow.

*Styles.*—Color: Reddish.

*Stigmas.*—Color: Greenish white.

Form: Bush.

Growth: Vigorous, dwarf, upright, branching.

Foliage:

*Number of leaflets on normal mid-stem leaves.*—5 or 7.

*Size.*—Small (2½"×2").

*Quantity.*—Abundant.

*Color.*—New foliage: Bronze. Old foliage: Dark glossy green.

Leaflets:

*Shape.*—Pointed oval.

*Texture.*—Upper side: Leathery, glossy.

*Edge.*—Serrated.

*Serration.*—Single, small.

*Petiole rachis.*—Color: Green.

*Petiole Underside.*—Rough with prickles and occasional glands.

*Stipules.*—Medium, bearded.

*Disease resistance.*—Resistant to mildew and rust under normal growing conditions at Somis, Calif. JACflare is susceptible to blackspot.

Wood:

*New wood.*—Color: Light green. Bark: Smooth.

*Old wood.*—Color: Green. Bark: Smooth.

Prickles:

*Quantity.*—On main canes from base: Ordinary. On laterals from main canes: Ordinary.

*Form.*—Medium, hooked slightly downward.

*Color when young.*—Red.

Small prickles:

*Quantity.*—On main stalks: Few. On laterals: Few.

I claim:

1. A new and distinct variety of rose plant of the miniature class, substantially as herein shown and described, characterized particularly as to novelty by the unique combination of its compact (2½×2 feet) habit of growth, dark green, glossy, leathery foliage, bright yellow flower color, continuous bloom, and resistance to powdery mildew and rust.

* * * * *

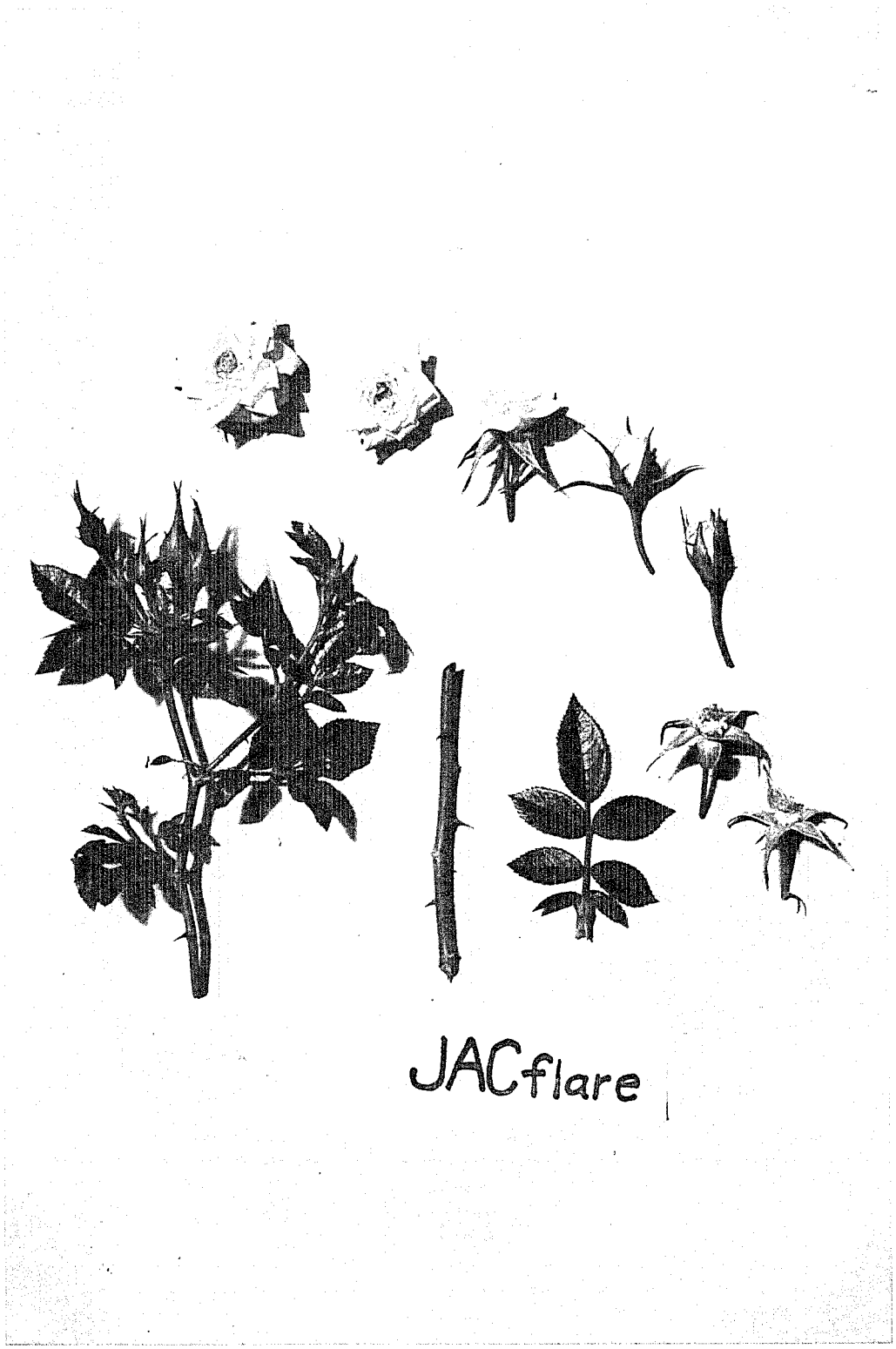
JACflare